April 24, 1962 D. D. BELCHER Plant Pat. 2,139

MAPLE TREE

Filed Dec. 2, 1960

INVENTOR.
Darrold D. Belcher

BY
Buckhorn, Cheatham & Blore

ATTORNEYS

United States Patent Office

Plant Pat. 2,139
Patented Apr. 24, 1962

2,139
MAPLE TREE

Darrold D. Belcher, 210 SE. Vista Ave., Gresham, Oreg.

Filed Dec. 2, 1960, Ser. No. 73,467
1 Claim. (Cl. 47—59)

The present invention relates to a new and distinct variety of maple tree, believed to be a variety of the sugar maple tree, *acer saccharum*.

The primary distinguishing characteristics of my variety of maple tree is the form of its leaf which is strikingly more deeply lobed than the leaf of the sugar maple tree. The leaf differences can best be defined by comparison to leaves of other maple trees.

My new variety of maple tree was found by me as a seedling in a nursery which is located near Gresham, Oregon and which contains many other trees and particularly sugar maple trees.

I have reproduced near Gresham, Oregon, the new variety asexually, specifically by removing buds from trees of my invention and budding them onto regular sugar maple trees. After the budding has taken, the upper part of the stock tree is removed. The characteristics of my tree have proved to be firmly fixed.

Figure 1:
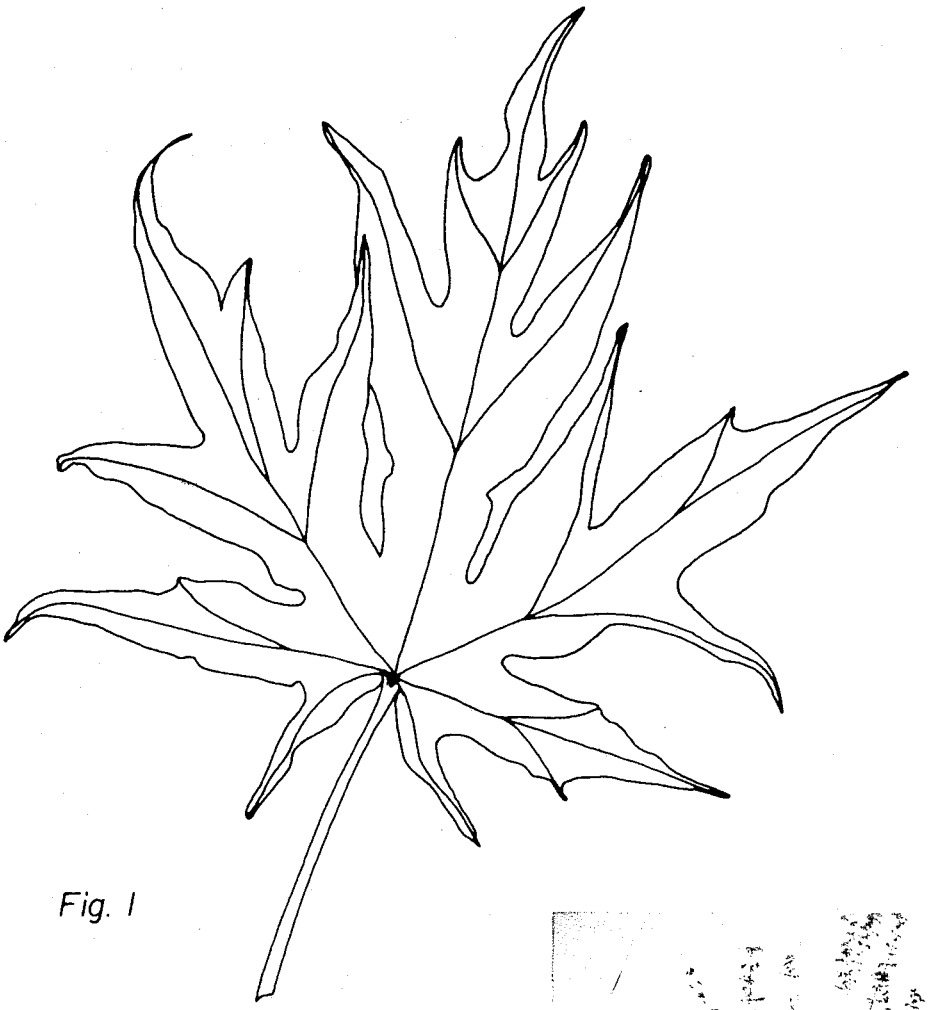
FIG. 1 is an outline of a typical leaf of a tree of my invention, some of the major veins being shown, the stem being shortened for convenience.
Figure 2:
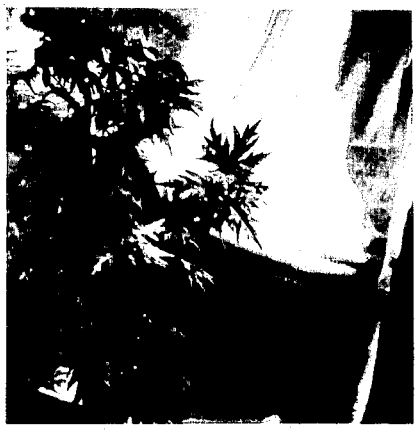
FIG. 2 is a color photograph of part of a tree of my invention.
Figure 3:
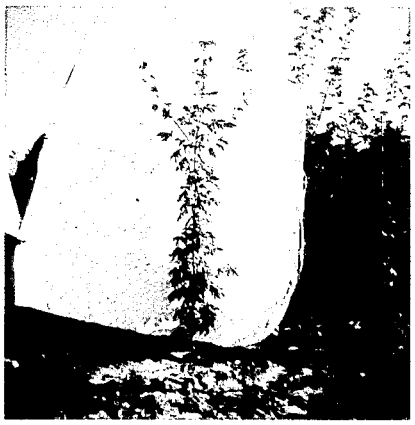
FIG. 3 is a color photograph of a two-year-old tree of my invention.

Referring to the drawings, a typical leaf outline is shown. While it is apparent by comparing the leaf of FIGURE 1 with the leaf of a sugar maple tree, that the leaf of the tree of my invention is derived from the leaf of the sugar maple tree, my leaf is much more deeply cleft and the lobes are considerably narrower than the lobes of a leaf of the sugar maple tree. The side lobes on the main lobes of my leaf are better developed and defined by deeper clefts than those of the leaf of the sugar maple tree. For instance, in the sugar maple leaf, the central main lobe has two definite side lobes, one on each side, and only the commencement of two other lobes in the form of bulges. In my leaf, the central main lobe has four well defined side lobes. This difference also exists between my leaf and that of the leaf of the Oregon maple, *acer macrophyllum*.

The leaf of my tree is also distinguished from other maple leaves, for instance, the silver maple tree, *acer saccharinum*, in that the marginal edges of the lobes of my leaf are relatively smooth (like the edges of the leaf of the sugar maple tree) whereas the margins of the lobes of the leaf of the silver maple tree are serrated. Also, the clefts of my leaf are deeper and the lobes better developed.

The color of my leaves in the spring, summer and fall is substantially the same as that of the sugar maple tree in the same periods.

In overall size, the leaves of my tree approximate those of the sugar maple tree, although some of the larger leaves of my tree may have a lateral span of twelve or more inches.

Following is a brief description of my new variety:

Tree: Upright, healthy.

Growth: Rapid and vigorous, attaining a height of 6 to 10 feet at two years. Somewhat similar to the sugar maple tree, but in many instances more vigorous.

Trunk: Similar in shape, form, coloration and appearance to that of the sugar maple tree.

Foliage:

*Size.*—Large. In first year trees budded on strong understock, the leaf size will be larger than on the same tree during its subsequent years of growth. For instance, on such a first year tree in September a smaller leaf will have a span of around 5 or 6 inches and a height from base to tip of around four inches, whereas the larger leaves vary from this size upward in excess of 12 inches in breadth and 8 or 9 inches and greater in height. The same tree, two or three years old, will have leaves of more normal size, around 3¼–5½ inches in breadth.

*Shape.*—Palmately divided, very deeply cleft with narrow lobes. The ratio of the height of the leaf from the base to the top tip in relation to the distance from the base to the level of the commencement of the main clefts for the central lobes varies roughly between a ratio of 5 to 1 and 8 to 1.

Color: Same as the sugar maple tree.

Having thus described my invention, I claim:

A new and distinct variety of sugar maple tree substantially as herein shown and described, characterized particularly as to novelty by having leaves similar to those of the sugar maple tree, but distinctly more deeply cleft and with narrower and better developed lobes.

No references cited.